United States Patent [19]

Wu

[11] Patent Number: 5,274,179
[45] Date of Patent: Dec. 28, 1993

[54] FLUORINATED PHOTOINITIATORS AND THEIR APPLICATION IN UV CURING OF FLUORINATED MONOMERS

[75] Inventor: Chengjiu Wu, Morris, N.J.

[73] Assignee: AlliedSignal Inc., Morristownship, Morris County, N.J.

[21] Appl. No.: 43,318

[22] Filed: Apr. 6, 1993

[51] Int. Cl.$^5$ .............................................. C07C 69/63
[52] U.S. Cl. .................................. 560/184; 560/138; 560/227; 568/331; 554/226; 554/213
[58] Field of Search ............... 568/331; 560/184, 138, 560/227; 554/213, 226; 522/42, 44

[56] References Cited

U.S. PATENT DOCUMENTS

| | | | |
|---|---|---|---|
| 3,937,722 | 2/1976 | Heine et al. | 568/331 |
| 4,144,156 | 3/1979 | Kuesters et al. | 568/331 |
| 4,861,916 | 8/1989 | Kohler et al. | 568/331 |
| 4,922,004 | 5/1990 | Kohler et al. | 568/331 |
| 4,950,795 | 8/1990 | Husler et al. | 568/331 |
| 5,202,359 | 4/1993 | McIntyre | 522/44 |

FOREIGN PATENT DOCUMENTS

| | | | |
|---|---|---|---|
| 0040923 | 12/1981 | European Pat. Off. | 560/184 |
| 0132869 | 2/1985 | European Pat. Off. | 560/184 |

OTHER PUBLICATIONS

Hult et al., "Photocuring in Air Using a Surface Active Photoinitiator", ACS Polymer Preprints, 25-1, 329 (1984).

Primary Examiner—James H. Reamer
Attorney, Agent, or Firm—Gerhard H. Fuchs; Richard C. Stewart

[57] ABSTRACT

Photoinitiators having at least one terminal fluoroalkyl moiety are useful for photopolymerizing and photocuring fluorinated as well as non-fluorinated monomers, especially fluorinated acrylic monomers.

11 Claims, No Drawings

FLUORINATED PHOTOINITIATORS AND THEIR APPLICATION IN UV CURING OF FLUORINATED MONOMERS

FIELD OF THE INVENTION

This invention relates to photoinitiators having a perfluoroalkyl moiety, which are useful for photopolymerizing and photocuring fluorinated as well as nonfluorinated monomers, especially fluorinated acrylic monomers.

BACKGROUND OF THE INVENTION

Printing inks, paints, and other coating materials usually are applied as a liquid layer, followed by curing or drying to the solid state. Curing or drying can occur by physical means such as evaporation or absorption of the solvent or dispersion medium, or by chemical reaction such as polymerization or cross-linking. Curing by UV irradiation-induced chemical reaction is particularly desirable for it avoids the need for solvents, thus eliminates potential safety hazards and reduces environmental pollution; it also speeds up production.

Photocuring coating compositions are usually comprised of three components: the monomer, a photoinitiator, and additives. The monomer is an unsaturated or cyclic organic compound which can undergo polymerization. It can be a single compound or a mixture of compounds. Typical monomers employed in photocuring coating compositions include styrene-unsaturated polyesters, acrylates, thiol-enes, allyl ethers, vinyl ethers, epoxides, and the like. The monomers are preferably bi- or multi-functional, to form a highly cross-linked network providing maximum strength and stability.

The photoinitiators are photosensitive compounds which absorb UV radiation and produce activated species—typically free radicals (for styrene, acrylate and allyl monomers) or cationic in nature (for vinyl ethers and epoxides)—to initiate polymerization or cross-linking. These photoinitiators can be used as a single compound or mixtures of different compounds, to meet desired curing characteristics.

The additives include the ususal pigments, dyes, inhibitors to prevent polymerization during storage, stabilizers to reserve optimum properties and prolong service life, regulators to adjust flow characteristics, and the like.

Acrylic coatings, including those based on mono- and multi-functional acrylates, methacrylates, and acrylic oligomers derived from epoxides, polyesters, and polyurethanes combine the advantages of superior film properties (clarity, strength, adhesion, gloss, etc.); adjustable flow properties for easy application; and rapid curing. Acrylic coatings based on fluoroalkyl acrylic ester monommers (herein sometimes referred to as "F-acrylates") possess highly desirable properties such as high thermal and chemical stablitity, low surface energy, low friction, and low refractive index. Such advantageous properties are dependent on fluorine content; they tend to improve with increasing fluorine content. For example, the refractive indix of amorphous flurocrylic polymers decreases with increasing length and number of the fluoroalkyl chains.

Unfortunately, the photoinitiators conventionally employed for polymerizing the usual acrylic monomers are not miscible with the highly fluorinated acrylate monomers, and there are no ready means for photocuring such acrylate monomers. UV curing of such fluorinated acrylate monomers without the aid of a photoinitiator, while feasible, gives less than optimum properties, is time consuming and expensive. This invention provides new photoinitiators which are compatible with highly fluorinated acrylate monomers.

SUMMARY OF THE INVENTION

In accordance with one aspect of this invention, there are provided fluorinated photoinitiators of the formula

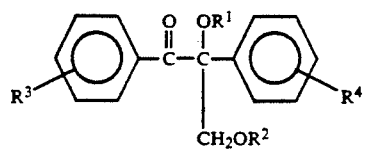
(I)

wherein
- $R^1$ and $R^2$ are independently selected from the group consisting of H; alkyl, straight chain, branched or cyclic, having from 1 to 40 carbons; and $-Y-R_F$;
- $R^3$ and $R^4$ are independently selected from the group consisting of H; alkyl, straight chain, branched or cyclic, having from 1 to 40 carbons; aryl; $-OY-R_F$; $-Y-R_F$; and $-R_F$; wherein
- Y in different $-OY-R_F$ and $-Y-R_F$ groups is independently $-C(O)-$; $-(CH_2)_k-$ wherein k is an integer of from 1 to 10; $-CH_2CH(OH)CH_2-$; and $-(CH_2CH_2O)-$; and
- $-R_F$ in different $-OY-R_F$, $-Y-R_F$ and $-R_F$ groups is independently $-(CF_2)_tZ$; $-CF(CF_3)[OCF_2CF(CF_3)]_mZ$; and $-CF_2(OCF_2CF_2)_m-(CF_2O)_nZ$; wherein t is an integer of from 1 to 20; m is an integer of from 1 to 20; n is an integer of from 1 to 20; and Z is H or F;

with the proviso that at least one of $R^1$ and $R^2$ is $-Y-R_F$.

The photoinitiators of formula (I), above, are suitable for photopolymerizing unsaturated monomers, especially fluorinated monomers, including fluorinated acrylic and perfluoroether monomer. The fluorinated acrylic monomers are well known compounds and include, but are not limited to, to fluoroacrylates of the formula $$R_F-X-A \qquad (II)$$

wherein
- $R_F$ is a per- or,polyfluorinated saturated, monovalent, nonaromatic, aliphatic radical which may be straight chain, branched or cyclic;
- A is an ethylenically unsaturated group selected from the group consisting of $-O-C(O)-CR=CH_2$; $-O-C(O)NH-(CH_2)_a-O-C(O)-CR=CH_2$; and $-O-C(O)NH-R'-NHC(O)O-(CH_2)_a-O-C(O)-CR=CH_2$;

wherein
- R is H or $CH_3$;
- a is an integer of from 2 to 6;
- R' is a divalent aliphatic or cycloaliphatic bridging group having 2 to 14 carbon atoms, or an aryl group having 6 to 14 carbon atoms; and
- X is a divalent bridging group selected from the group consisting of $-SO_2-N(R'')-(CH_2)_b-$; $-(CH_2)_{b^1}-$; and $-C(O)-N(R'')-(CH_2)_b-$ wherein b is an integer of from 2 to 12;
b¹ is an integer of from 1 to 12;
R" is H; lower alkyl having 1 to 4 carbons; or —(CH$_2$)$_c$—Z wherein Z is as described above and c is 2 or 3;
with the proviso that when R" is —(CH$_2$)$_c$—Z, then b is 2 or 3, and with the further proviso that when R$_F$ contains 6 or more carbon atoms there are no more than 6, 10 or 20 atoms respectively in the chain between R$_F$ and the ester oxygen of the acrylate or methacrylate group. For a more detailed description of the acrylic monomer of formula (II), above, and specific preferred embodiments encompassed within this formula, reference is made to U.S. Pat. No. 4,985,473 issued 15 Jan. 1991 to Williams et al.

Further monomers suitable for actinic-radiation induced polymerization utilizing the above-described fluorinated photoinitiators include, but are not limited to, those having the formula (III) Z—R$_F^2$—Y—(A)$_n$ wherein
A is as defined in connection with Formula II, above;
Y is —(CH$_2$)$_{b^1}$—, —C(O)—N(R$^2$)—(CH$_2$)$_b$— or
—CH$_2$—CH—CH$_2$— wherein
b is an integer of from 2 to 12;
b¹ is an integer of from 1 to 12;
R² is hydrogen or alkyl having 1 to 4 carbon atoms (preferably methyl or ethyl) or —(CH$_2$)$_c$—A wherein A is as defined in connection with formula II, above, and c is an integer of from 2 to 3, with the proviso that when R² is —(CH$_2$)$_c$—A, then b is 2 or 3;
R$_F^2$ is a divalent poly(fluorooxyalkylene) group having a number average molecular weight from about 500 to 20,000, or higher, and preferably of from about 1,000 to about 10,000; and
is CF$_3$O—, CF$_3$OCF(CF$_3$)O—, or —Y—A wherein Y and W are as defined in connection with formula II, above.
R$_F^2$ desirably comprises highly fluorinated polyethers having randomly distributed units of the formula —CF$_2$O—, —CF$_2$CF$_2$O— and —C$_3$F$_6$O—, and may also have incorporated therein groups of the formula —CF$_2$—CF$_2$—CF$_2$—CF$_2$O—, —CF$_2$— and —C$_2$F$_4$—, all as described in U.S. Pat. No. 4,985,473 issued 15 Jan. 1991 to Wiliams et al.

DETAILED DESCRIPTION OF THE INVENTION

The following detailed description sets forth the preferred embodiments and the best mode presently contemplated for its practice.

The above-described fluorinated photoinitiators (herein also referred to as "F-photoinitiators") are based on known fluorine-free photoinitiators of the aromatic ketone type. A fluorine-containing moiety having a terminal fluoroalkyl group is attached to the photoinitiator by reacting functional group(s) in the fluorinated molecule with functional group(s) of the photoinitiator or its precursor in such a way that the connection will not significantly depress the photon-absorption and radical-formation characteristics. The fluorine-free photoinitiators are well known for vinyl and acrylate polymerization.

Selection of the mono or multiple functionalized fluoroalkyl starting materials for providing the fluorine-containing moiety for the F-photoinitiators is, inter alia, based on consideration of the reactivities of their functional groups. Suitable functional groups may include, but are not limited to, hydroxy, acyl fluoride, acyl chloride, carboxyl, halogen (bromide and iodide), isocyanate, and epoxy groups. The connecting linkage may be direct C—C bonding, or an ester or ether linkage. For improved processibility, a branched fluoroalkyl chain containing 5-20 carbons and some etheric linkages is preferred. If the fluoroalkyl chain is short (contains about 3 to about 7 carbon atoms), then the F-photoinitiators are soluble in normal acrylate system and can act as a surface-active initiators, as to be described in more detail, infra. When the fluoroalkyl chain is long (contains more than about 6 carbon atoms), then the F-photoinitiators are soluble and photoactive in highly fluorinated acrylic monomers of the type described, supra.

The method for making these F-photoinitiators depends on the type of linkage by which the fluorinated moiety is attached to the aromatic ketone. The term "photoinitiator", as used in the following description, refers to the non-fluorinated aromatic ketone starting material.

F-photoinitiators having an ester linkage can be made by esterification of fluorinated carboxylic acids (carboxylic acid with a fluoroalkyl group) with hydroxyl functionalized photoinitiators. The hydroxyl group may be attached to the α-, β- or more remote positions of the aromatic ketone moiety. We found the F-photoinitiators made by esterification at α-position are less reactive than at the β-or more remote positions unless a hydrogen donating compound such as an amine is co-existing with the former. The esterification can be performed in an aprotic solvent, such as methylene chloride, and in the presence of an acid absorber, preferably a tertiary amine such as triethylamine. The reaction is usually run at room temperature. The esterification process may be exemplified by the following scheme:

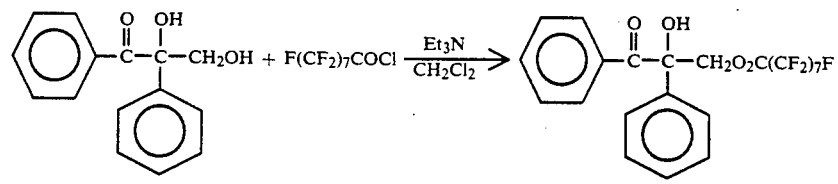

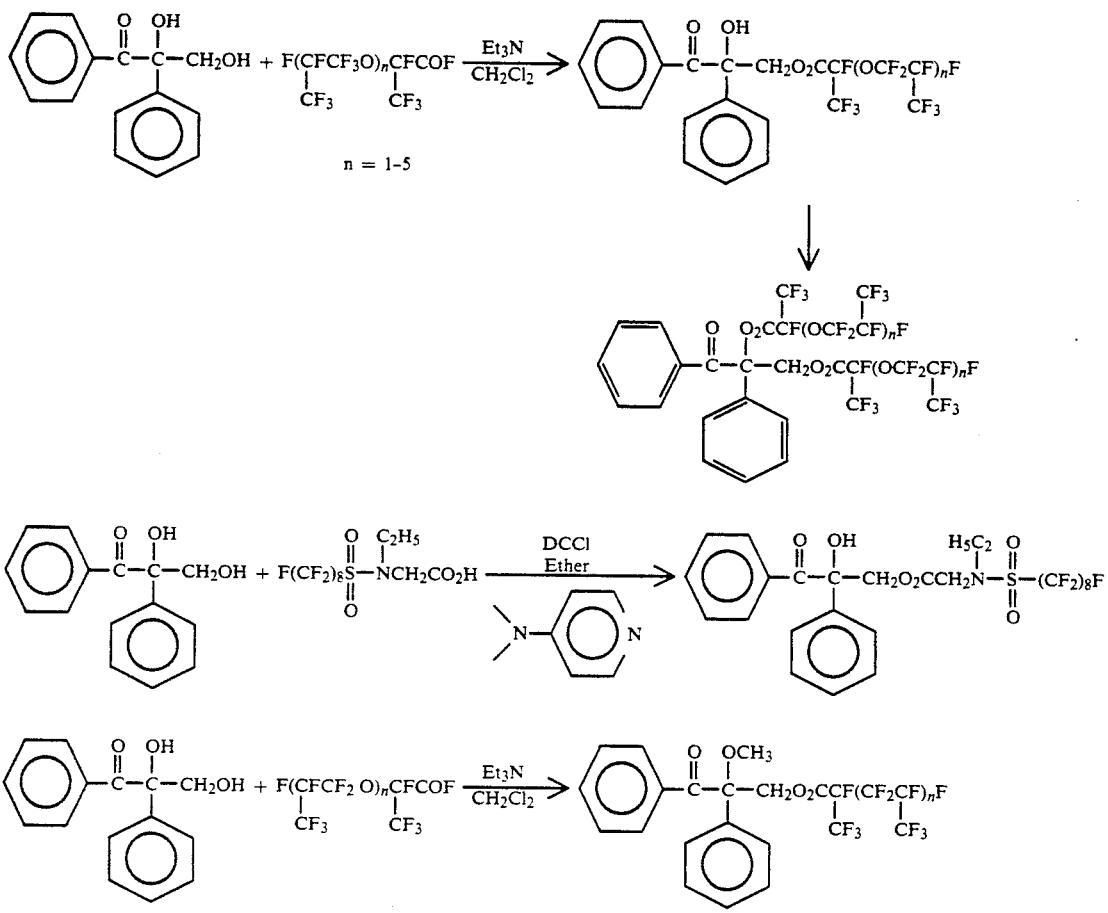

F-Photoinitiators having an ether linkage can be made by reacting a hydroxyl functionalized photoinitiator with a fluoroalkyl terminated alkyl halide, preferably a bromide or iodide, more preferably an iodide, or by reacting the hydroxyl group with a fluoroalkylepoxide. The process for making these ether type products may be exemplified by the following scheme:

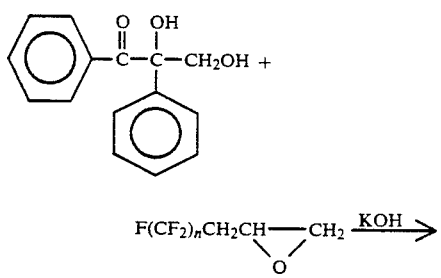

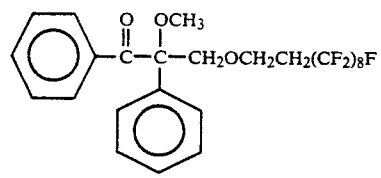

F-photoinitiators in which the fluoroalkyl is attached through C—C bonding can be made by methods exemplified by the following scheme:

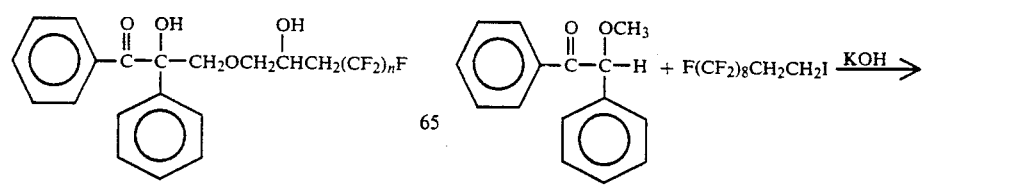

-continued

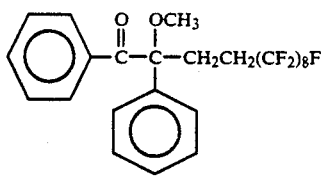

The methods involved in attaching the fluorinated moiety to the above described aromatic ketone type photoinitiators to obtain the F-photoinitiators follow procedures conventionally employed in organic synthesis and are well known to those skilled in the art.

The examples set forth below further illustrate the invention and set forth the best mode presently contemplated for its practice

EXAMPLE 1

Preparation of the compound

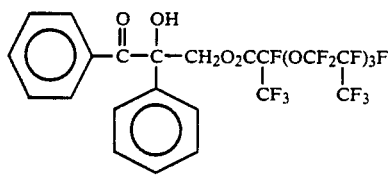

To a stirred mixture of 4.8 parts of α-hydroxymethyl benzoin, 2.3 parts of triethylamine, and 20 parts of methylene chloride at room temperature was slowly added 14 parts of perfluoro-2,5,8-trimethyl-3,6,9-trioxadodecanoyl fluoride (HFPO tetramer, acid fluoride) dissolved in 5 parts of 1,1,2-trichlorotrifluoroethane over a 2 hour period. After stirring for another two hours, the reaction mixture was washed four times with 200 parts of saturated saline solution and dried over anhydrous magnesium sulfate. The viscous liquid remaining after removal of the solvent was chromatographed on a silica gel column using a 1:2 methylene chloride-hexane mixture as eluent to give 18 parts of a viscous, pale liquid product. Its structure was consistent with the above formula, as confirmed by proton, carbon-13 and fluorine NMR, as well as by mass spectra.

EXAMPLE 2

Preparation of Compound

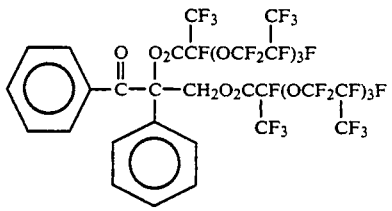

To a stirred mixture of 4.8 parts of α-hydroxymethyl benzoin, 2.3 parts of triethylamine, and 20 parts of methylene chloride at room temperature was slowly added 30 parts of perfluoro-2,5,8-trimethyl-3,6,9-trioxadodecanoyl fluoride (HFPO tetramer, acid fluoride) dissolved in 10 parts of 1,1,2-trichlorotrifluoroethane over a 2 hour period. After stirring for another two hours, the reaction mixture was loaded on top of a silica gel packed column and eluted with a 1:5 methylene chloride-hexane mixture to give 25 parts of a viscous, pale liquid product, having the above structure as confirmed by proton, carbon-13 and fluorine NMR, as well as by mass spectra.

EXAMPLE 3

Preparation of the compound

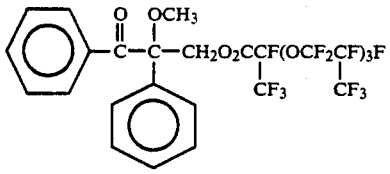

To a stirred mixture of 3.2 parts α-hydroxymethyl benzoin methyl ether, 2.5 parts of triethylamine, 20 parts of methylene chloride and 20 parts of 1,1,2-trichlorotrifluoroethane was slowly added 10 parts of perfluoro-2,5,8-trimethyl-3,6,9-trioxadodecanoyl fluoride (HFPO tetramer, acid fluoride) dissolved in 10 parts of 1,1,2-trifluorotrichloroethane during a 0.5 hour period. After stirring overnight, the reaction mixture was washed four times with 50 parts of saturated saline solution and dried over anhydrous magnesium sulfate. The viscous liquid (8.0 parts) remaining after removing the solvent by evaporation was chromatographed on a silica gel column using 1,1,2-trifluorotrichloroethane as eluent to give 3.6 parts of pure product which is a viscous and pale yellow liquid. Its structure was consistent with the above formula, as confirmed by proton, carbon-13 and fluorine NMR, as well as by mass spectra.

EXAMPLE 4

Preparation of the compound

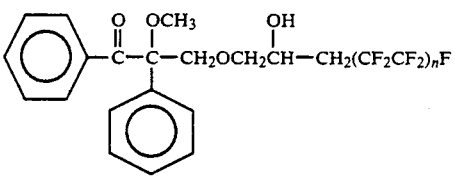

To a stirred solution of 2.0 parts of α-hydroxymethyl benzoin methyl ether in 15 parts by volume of N,N-dimethylforamide at room temperature is added in portions 0.3 part of sodium hydride. After 1 hour, 5.0 parts of fluoroalkylepoxide having the formula

$F[CF_2CF_2]_nCH_2CHCH_2O$ (n=2-20) (duPont's "Zonyl ® BA Fluoroalkylepoxide") is added and the reaction mixture is gently warmed to reflux. After cooling, the mixture is poured into water and extracted with 1,1,2-trichlorotrifluoroethane. The solution is loaded on a chromatograph column packed with silica gel and eluted with a solvent mixture of 1:2 1,1,2-trichlorotrifluoro ethane and hexane to obtain the desired product.

EXAMPLE 5

Preparation of the compound

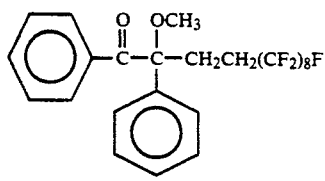

To a stirred suspension of 2.2 parts of benzoin methyl ether and 0.8 part of potassium hydroxide in 15 parts by volume of N,N-dimethylformamide at room temperature is added 7.0 parts of 1-iodo-1H,1H,2H,2H-perfluorooctane and the reaction mixture is gently warmed. After cooling, the mixture is poured into water and extracted with 1,1,2-trichlorotrifluoroethane. The solvent is removed by evaporation, and the remainder is loaded on a chromatograph column packed with silica gel and eluted with a solvent mixture of 1:2 1,1,2-trichlorotrifluoro-ethane and hexane to obtain the desired product.

EXAMPLES 6–18

Photocuring compositions are prepared by dissolving F-photoinitiators of the present invention in fluoroacrylic monomers. The resultant compositions are spread on a glass substrate to form an about 10 μm thick layer (unless otherwise indicated), followed by subjecting the layer under nitrogen cover to UV radiation from a medium pressure mercury lamp at an intensity of 25 mW/cm$^2$. The components of these compositions, their weight proportions, and the results obtained are summarized, infra.

| Example 6 | |
| --- | --- |
| F-Photoinitiator (A): | Product of Example 1 |
| Monomer (B): | $[CH_2=CHC(O)OCH_2CF(CF_3)-O-\{CF(CF_3)CF_2O\}_2C_2F_4]_2$ |
| Ratio A:B | 2:98 |
| Result: | This composition was spin-coated in a 2 μm thick layer. Irradiation was under nitrogen cover. Complete cure was achieved after exposure of one minute. |
| Example 7 | |
| F-Photoinitiator (A): | Product of Example 1 |
| Monomer (B): | $CH_2=CHC(O)OCH_2-(C_2F_4O)_m-(CF_2O)_n-CH_2OC(O)CH=CH_2$ wherein m/n is about 0.8, and the molecular weight is about 2,000. |
| Ratio A:B | 2:98 |
| Result: | This composition was spin-coated in a 5–10 μm thick layer. Irradiation was under nitrogen cover. Complete cure was achieved after exposure of one minute. |
| Example 8 | |
| F-Photoinitiator (A): | Product of Example 2 |
| Monomer (B): | $CH_2=CHC(O)OCH_2(CF_2)_4CH_2OC(O)CH=CH_2$ |
| Ratio A:B | 1:99 |
| Result: | No curing occurred after one minute's exposure. |
| Example 9 | |
| F-Photoinitiator (A): | 1 Part product of Example 2 plus 1 part N,N-dimethylaniline |
| Monomer (B): | $CH_2=CHC(O)OCH_2(CF_2)_4CH_2OC(O)CH=CH_2$ |
| Ratio A:B | 1:99 |
| Result: | Complete cure was achieved after an exposure of 1 minute. |
| Example 10 | |
| F-Photoinitiator (A): | Product of Example 3 |
| Monomer (B): | $CH_2=CHC(O)OCH_2-(C_2F_4O)_m-(CF_2O)_n-CH_2OC(O)CH=CH_2$ wherein m/n is about 0.8, and the molecular weight is about 2,000. |
| Ratio A:B | 2:98 |
| Result: | This composition was spin-coated in a 5–10 μm thick layer. Irradiation was under nitrogen cover. Complete cure was achieved after exposure of one minute. |

EXAMPLES 11–18

The procedure of Example 6 is repeated except for use of a mixture of acylates as monomer B. Curing is achieved in each case.

EXAMPLE 11

The procedure of Example 6 is repeated except for use of a 1:1 mixture of $CH_2=CHC(O)OCH_2(CF_2)_4CH_2OC(O)CH=CH_2$ and $[CH_2=CHC(O)OCH_2CF(CF_3)-O-\{CF(CF_3)CF_2O\}_2C_2F_4]_2$. Curing is achieved.

EXAMPLE 12

The procedure of Example 6 is repeated except for use of a 1:1 mixture of $[CH_2=CHC(O)OCH_2CF(CF_3)-O-\{CF(CF_3)CF_2O\}_2C_2F_4]_2$ and $CH_2=CHC(O)OCH_2-(C_2F_4O)_m-(CF_2O)_n-CH_2OC(O)CH=CH_2$ wherein m/n is about 0.8, and the molecular weight is about 2,000. Curing is achieved.

EXAMPLE 13

The procedure of Example 6 is repeated except for use of a 1:1 mixture of $[CH_2=CHC(O)OCH_2CH_2C_7F_{17}$ and $CH_2=CHC(O)OCH_2-(C_2F_4O)_m-(CF_2O)_n-CH_2OC(O)CH=CH_2$ wherein m/n is about 0.8, and the molecular weight is about 2,000. Curing is achieved.

EXAMPLE 14

The procedure of Example 6 is repeated except for use of a 65:35 mixture of $CH_2=CHC(O)OCH_2(CF_2)_4CH_2OC(O)CH=CH_2$ and $CH_2=CHC(O)OCH_2CH_2N(C_2H_5)SO_2C_8F_{17}$. Curing is achieved.

EXAMPLE 15

The procedure of Example 6 was repeated except for substitution of the fluorinated methacrylate $CH_2=C(CH_3)CO(O)CH_2C_7F_{15}$ for the $[CH_2=CHC(O)OCH_2CF(CF_3)-O-\{CF(CF_3)CF_2O\}_2C_2F_4]_2$. Curing is achieved.

EXAMPLE 16

The procedure of Example 6 was repeated except for use of a 65:35 mixture of $[CH_2=CHC(O)OCH_2CF(CF_3)-O\{CF(CF_3)CF_2O\}_2C_2F_4]_2$ and $CH_2=C(CH_3)CO(O)CH_2CH_2N(C_2H_5)SO_2C_8F_{17}$. Curing is achieved.

EXAMPLE 17

The procedure of Example 6 is repeated except for use of a 1:1 mixture of $[CH_2=CHC(O)OCH_2CF(CF-$ 3)—O—{CF(CF$_3$)CF$_2$O}$_2$C$_2$F$_4$}$_2$ and CH$_2$=CHCO(O)CH$_2$C$_7$F$_{15}$. Curing is achieved.

EXAMPLE 18

The procedure of Example 17 is repeated except for use of a 1:1 mixture of [CH$_2$=CHC(O)OCH$_2$CF(CF$_3$)—O—{CF(CF$_3$)CF$_2$O}$_2$C$_2$F$_4$]$_2$ and CH$_2$=C(CH$_3$)CO(O)CH$_2$C$_7$F$_{15}$. Curing is achieved.

The F-photoinitiators of the present invention are employed in the amounts in which conventional photoinitiators are typically employed for curing acrylates, say in amounts in the order of from about 0.2 to about 5 weight percent of the combined weight of initiator and monomer.

With respect to the photoinitiators of formula (I), supra, the following represent preferred embodiments:

In the R$_f$ groups, Z is preferably fluorine. When R$_f$ is —(CF$_2$)$_t$Z, then t preferably is an integer of at least 7, more preferably an integer of from about 7 to about 20, if the photoinitiator is intended for curing fluorine-containing acrylic monomers. If the photonitiator is intended for curing non-fluorinted acrylic monomers, then t preferably is an integer from about 1 to about 7. When R$_f$ is —CF(CF$_3$)[OCF$_2$CF(CF$_3$)]$_m$Z, or —CF$_2$—(OCF$_2$CF$_2$)$_m$—(OCF$_2$)$_n$Z, then m preferably is an integer of from about 2 to about 20, and n is an integer of from about 1 to about 40, more preferably from about 1 to about 20.

The R$^1$ and R$^2$ groups are preferably H or alkyl having from 1 to 40 carbons, more preferably from 1 to 10 carbons. Specific examples of preferred embodiment are the methyl, ethyl, propyl etc. groups; H and methyl are most preferred.

Y is preferably —C(O)—; —(CH$_2$)$_k$—wherein k is an integer of from 1 to 4; and —(CH$_2$CH$_2$O)—.

The R$^3$ and R$^4$ groups are preferably H, —OY—R$_F$ and —Y—R$_F$.

I claim:

1. Compounds of the formula

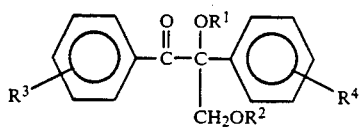

wherein
R$^1$ and R$^2$ are independently selected from the group consisting of H; alkyl, straight chain, branched or cyclic, having from 1 to 40 carbons; and —Y—R$_F$;
R$^3$ and R$^4$ are independently selected from the group consisting of H; alkyl, straight chain, branched or cyclic, having from 1 to 40 carbons; aryl; —OY—R$_F$; —Y—R$_F$; and —R$_F$;
wherein
Y in different —OY—R$_F$ and —Y—R$_F$ groups is independently —C(O)—; —(CH$_2$)$_k$—wherein k is an integer of from 1 to 10; —CH$_2$CH(OH)CH$_2$—; and —(CH$_2$CH$_2$O)—; and
—R$_F$ in different —OY—R$_F$, —Y—R$_F$ and —R$_F$ groups is independently —(CF$_2$)$_t$Z; —CF(CF$_3$)[OCF$_2$CF(CF$_3$)]$_m$Z; and —CF$_2$(OCF$_2$CF$_2$)$_m$—(CF$_2$O)$_n$Z; wherein
t is an integer of from 1 to 10; m is an integer of from 1 to 10; n is an integer of from 1 to 10; and Z is H or F;
with the proviso that at least one of R$^1$ and R$^2$ is —Y—R$_F$.

2. Compounds of claim 1 wherein R$_F$ includes a —(CF$_2$)$_t$Z moiety wherein t is an integer greater than 7.

3. Compounds of claim 1 wherein R$_F$ includes a moiety selected from the group consisting of —CF(CF$_3$)[OCF$_2$CF(CF$_3$)]$_m$Z and —CF$_2$(OCF$_2$CF$_2$)$_m$—(CF$_2$O)$_n$Z wherein m and n each are integers of from 1 to 10.

4. Compounds according to any one of claims 1, 2 or 3 wherein Z in the —R$_F$ moiety is F.

5. Compounds according to claim 1 wherein the R$^1$ and R$^2$ groups are H or alkyl, straight chain, branched or cyclic, having from 1 to 10 carbon atoms.

6. Compounds of claim 5 wherein R$_F$ includes a —(CF$_2$)$_t$F moiety wherein t is an integer greater than 7.

7. Compounds of claim 5 wherein R$_F$ includes a moiety selected from the group consisting of —CF(CF$_3$)[OCF$_2$CF(CF$_3$)]$_m$F and —CF$_2$(OCF$_2$CF$_2$)$_m$—(CF$_2$O)$_n$F wherein m and n each are integers of from 1 to 10.

8. Compounds according to claim 1 wherein the R$^3$ and R$^4$ groups are selected from the group consisting of H, —OY—R$_F$ and —Y—R$_F$ wherein Y is selected from the group consisting of —C(O)—, —(CH)$_k$— wherein k is an integer of from 1 to 4, and —(CH$_2$CH$_2$O)—.

9. Compounds according to claim 8 wherein the R$^1$ and R$^2$ groups are H or alkyl, straight chain, branched or cyclic, having from 1 to 10 carbon atoms.

10. Compounds according to any one of claims 8 or 9 wherein R$_F$ includes a —(CF$_2$)$_t$F moiety wherein t is an integer greater than 7.

11. Compounds according to any one of claims 8 or 9 wherein R$_F$ includes a moiety selected from the group consisting of —CF(CF$_3$)[OCF$_2$CF(CF$_3$)]$_m$F and —CF$_2$(OCF$_2$CF$_2$)$_m$—(CF$_2$O)$_n$F wherein m and n each are integers of from 1 to 10.

* * * * *